United States Patent [19]

Virtanen et al.

[11] Patent Number: 5,536,526
[45] Date of Patent: Jul. 16, 1996

[54] XYLITOL-BASED BINDING AND DILUTING AGENT AND A PROCESS FOR THE PRODUCTION THEREOF

[75] Inventors: Jouko Virtanen; Matti Makela, both of Kantvik, Finland

[73] Assignee: Cultor Ltd., Helsinki, Finland

[21] Appl. No.: 79,794

[22] Filed: Mar. 20, 1991

Related U.S. Application Data

[63] Continuation-in-part of Ser. No. 314,766, Feb. 23, 1989, abandoned.

[30] Foreign Application Priority Data

Feb. 25, 1988 [FI] Finland .................................. 88092

[51] Int. Cl.$^6$ ............................................... A23G 3/00
[52] U.S. Cl. ........................................... 426/658; 426/660
[58] Field of Search ............................... 536/1.1; 514/23; 426/3, 4, 5, 6, 658, 660

[56] References Cited

U.S. PATENT DOCUMENTS 5,385,749  1/1995  Serpelloni et al. ................... 426/658

FOREIGN PATENT DOCUMENTS

| 193651 | 9/1986 | European Pat. Off. |
| 2336123 | 7/1977 | France. |
| 2380777 | 9/1978 | France. |
| 1526020 | 9/1978 | United Kingdom. |

*Primary Examiner*—Raymond Henley, III
*Attorney, Agent, or Firm*—Baker & McKenzie

[57] ABSTRACT

The present invention relates to a free flowing, compressible granulate which contains from 94% to 98% by weight of xylitol, another physiologically acceptable polyol such as mannitol, lactitol, maltitol or isomalt and less than 1% by weight of water.

9 Claims, No Drawings

XYLITOL-BASED BINDING AND DILUTING AGENT AND A PROCESS FOR THE PRODUCTION THEREOF

This is a continuation-in-part of application Ser. No. 07/314,766 filed Feb. 23, 1989, now abandoned.

TECHNICAL FIELD

This invention relates to a free flowing, compressible granulate which contains xylitol in combination with another polyol, preferably sorbitol. The composition of the instant invention is particularly suitable for use in the manufacture of tablets by direct compression means. The present invention also contemplates a method for the production of a free flowing, compressible granulate containing xylitol and another polyol (preferably sorbitol) which is suitable for use in the manufacture of tablets by direct compression means.

BACKGROUND OF THE INVENTION

A. The Advantages of Xylitol

The most commonly used sweetener for food and pharmaceutical contexts is sucrose. Sucrose is used for its well-known sweetening properties and also for bulking purposes. Although a wide variety of alternate sweeteners are available, sucrose is generally considered to be the optimum sweetener with regard to taste profile and technological properties. However, sucrose has been implicated as a contributory factor in many diseases including hypertension, coronary heart disease, arterial sclerosis and dental caries. These health concerns have led health care professionals to analyze the effects of sucrose and its prominent role in the diet.

Perhaps the most significant, well-documented effect of sucrose is its contribution to tooth decay. The mouth contains a number of bacterial strains which ferment common dietary carbohydrates such as sucrose. This fermentation generates acid as an end product which lowers the pH in the mouth; the lowered pH leads to a demineralization of tooth enamel and finally to the formation of dental lesions or caries.

It is well known that it is not the total quantity of sugar consumed per se, but the frequency of consumption that contributes to dental caries. Thus, the presence of sucrose and other fermentable carbohydrates in regular meals is not the principal cause of tooth decay. The consumption of fermentable carbohydrates between meals in the form of confections and sweetened pharmaceuticals (and the frequency of such consumption) have been shown to have a close relationship to the formation of dental caries. Long after the candy or drug has been consumed, the fermentable carbohydrate stays in the mouth and is fermented by *Streptococcus mutans* and other cariogenic bacteria, lowering the mouth pH and promoting dental caries as described above.

One approach to fighting dental caries is to reduce or eliminate the amount of fermentable carbohydrates such as sucrose in pharmaceutical or food contexts. The replacement of fermentable carbohydrates by sugar substitutes which cannot be fermented, or are less easily fermented by *S. mutans* and other bacteria has been shown to decrease the development of dental caries.

Xylitol has been used as a sugar substitute in certain contexts (e.g. chewing gum: U.S. Pat. No. 4,514,422 (Yang) and U.S. Pat. No. 3,422,184 (Patel)) with practical and commercial success. The use of xylitol is attractive because of its taste and technological advantages. Xylitol is a naturally occurring five carbon sugar alcohol which has the same sweetness as sugar and a caloric content which is less than that of sugar. Xylitol is found in small amounts in many fruits and vegetables and is produced in the human body during normal metabolism. Xylitol is particularly attractive because of its known metabolic, dental and technical characteristics.

From a metabolic perspective, xylitol is metabolized largely independent of insulin, so it can be safely consumed by non-insulin dependent diabetics. Further, xylitol has been shown to delay gastric emptying and to possibly suppress food intake which means it may have an important role in weight reducing diets.

A significant advantage of xylitol is that it is not fermented by *S. mutans* and other bacteria found in the mouth and, therefore, does not produce acids which, as described herein, contribute to the formation of dental caries. Xylitol is well established as a non-cariogenic substance, i.e. xylitol does not contribute to caries formation. Significant data also exists which supports the view that xylitol is not only non-cariogenic, but actively suppresses the formation of new caries and may even reverse existing lesions by inducing remineralization, i.e. it is a cariostatic material. A summary of clinical data regarding the effects of xylitol and its possible mechanisms is set forth in Bar, Albert, Caries Prevention With Xylitol: A Review of the Scientific Evidence, 55 Wld. Rev. Nutr. Diet. 183–209 (1983). The mechanism or mechanisms by which xylitol effects any cariostatic properties is not yet known, but some possible mechanisms which have been suggested include a reduction of oral levels of *S. mutans*, a reduction in the development of plaque, the stimulation of the flow of protective saliva, the favorable alteration of the composition of saliva, the retardation of demineralization and an enhancement of remineralization of tooth enamel.

Xylitol also has significant technological advantages, particularly with respect to taste profile. Xylitol produces a pleasant cooling effect in the mouth when consumed in the crystalline state. The energy required to dissolve one gram of xylitol is 34.6 calories, the highest known value for sugars and sugar alcohols; this produces a physical cooling effect which is desirable in many contexts. Xylitol is as sweet as sugar and does not typically manifest unpleasant aftertastes.

Other polyols, such as sorbitol, mannitol, lactitol and others have also been substituted for sucrose in a variety of contexts. All of these polyols have certain advantages—such as non-cariogenicity—over sucrose. However, none of the other polyols have been demonstrated to have a cariostatic effect.

One context in which xylitol has been heretofore utilized with only limited success is as a constituent in tablets. In pharmaceutical contexts, tablets are used for bringing active substances into a size, shape and texture that can be dosaged, chewed, sucked, swallowed whole or dissolved in water for drinking. In food contexts, tablets can take the form of compressed, fruit or mint flavored confections which consist of a sweetener(s), flavor(s) and optionally color and acid. Because of its taste and cariostatic properties as described above, xylitol is a potentially attractive constituent in tablets for both food and pharmaceutical purposes. Xylitol has not been extensively utilized as a binding or diluting agent in this context.

Sweetness in pharmaceutical tablets fulfills the purpose of making the product more pleasant to eat and to mask any unpleasant taste of the active ingredient(s). Today, many pharmaceutical tablets are sweetened with sucrose, lactose and other fermentable carbohydrates which are also used as diluents. Replacing sucrose and other fermentable carbohydrates with xylitol in those applications which must be sweetened would eliminate the use of cariogenic formulations in medicaments such as throat lozenges, cough tablets, vitamins, chewable tablets and others, and also takes advantage of the other attributes of xylitol discussed above, such as its noted cooling effect and metabolic characteristics.

In food contexts, tablets are usually sucked or chewed by the user and are often used as breath mints. Sucrose is the sweetener of choice in these contexts and has bulking properties as well. Replacing sucrose with xylitol would enable tablets to exploit the unique advantages of xylitol, particularly its anti-caries properties, and its pronounced cooling effect.

The cariostatic effect of xylitol is particularly important because clinical studies have shown that it is not the quantity of sucrose (or other acid producing substances such as maltose, lactose and dextrose), but the frequency of sucrose intake that is critical for caries development. Many pharmaceutical and food tablets are designed to be and are consumed at frequent and/or regular intervals throughout the day. For this reason, some dental researchers have suggested switching from sucrose, maltose, lactose, dextrose to a non-acid producing sweetener such as xylitol in pharmaceutical and food contexts.

B. Tableting Techniques and Tablets

Tablets can be formed by compression or by molding.

Modern compression tableting techniques—irrespective of the type (and ultimate shape of the end product)—utilize a piston like device with three stages in each cycle: (1) filling—adding the constituents of the tablet to the compression chamber; (2) compression—forming the tablet; and (3) ejection—removing the tablet. The cycle is then repeated. A representative tablet press is a MANESTY Novapress, manufactured by Manesty Machines Ltd., Liverpool, England, and many others are available.

Because many materials have some, or none, of the required qualities of "flowability" and "compressibility", binding and diluting agents have been developed to permit direct compression to take place. An ideal binding and diluting agent also functions in the tablet either as an active ingredient or as an agent which contributes or improves flavor or other properties. In this context, free flowing means that the particles to be compressed must enter the compression chamber as discreet particles; compressible means the particles form a tablet after compression and do not remain in a powdered or substantially powdered form.

Two critical criteria in the quality of a tablet are crushing strength (or hardness) and friability. The resistance of the tablet to chipping, abrasion, or breakage under conditions of storage, transportation and handling before usage depends on its hardness. Hardness is measured by determining lateral breaking strength (expressed in kilo ponds ("Kp"), Strong Cobb Units wherein 1 kp=1.4 S.C.U.) or Newtons ("N") wherein 10 S.C.U.=70N exerted on a single tablet at the moment of rupture. A representative hardness tester is the Model HT-300 manufactured by Key International, Inc. Acceptable hardness depends on the desired mouthfeel and the expected end use and packaging conditions of the tablet, but in most contexts, tablet hardness must be greater than about 10 S.C.U. to be commercially useful.

Friability is also a standard test known to one skilled in the art. Friability is measured under standardized conditions by weighing out a certain number of tablets (generally 20 or more), placing them in a rotating plexiglass drum in which they are lifted during replicate revolutions by a radial louver, and then dropped through the diameter of the drum. After replicate revolutions, the tablets are reweighed and the percentage of powder "rubbed off" or broken pieces is calculated. Friability in the range of about 0% to 3% is considered acceptable for most drug and food tablet contexts. Friability which approaches 0% is particularly preferred.

Tablets of insufficient hardness exhibit capping and/or lamination and can easily break apart or disintegrate under normal handling and packaging conditions. Tablets of insufficient hardness cannot be used for lozenges or mints which are designed to be sucked in the mouth, releasing the active ingredient(s) or flavor over time, and may have an undesirable powdery, grainy or coarse mouthfeel.

Sweet carbohydrates such as sugars and sugar alcohols are well suited for use as binding and diluting agents, particularly because they can function as an active ingredient or as a flavor improving agent. However, crystalline or powdered sugars and sugar alcohols as such are poorly suited for direct compression techniques because they have poor flowability and/or compressibility. Therefore, granulated sugars or sugar alcohols have been developed for use in direct compression. In pharmaceutical and food industries, granulated forms can be regarded as semi-finished products which are utilized as raw materials in effective tableting techniques.

The prior art discloses binding and diluting agents which contain sugars. For example, commercial binding and diluting agents include an agglomerated dextrose product sold under the trademark EMDEX, an agglomerated sucrose product containing dextrines sold under the trademark DIPAC and a pregelatinized directly compressible starch and mannitol product sold under the trademark STARCH 1500. Finnish Patent Application No. 854,885 discloses a fructose-based binding and diluting agent namely, a fructose agglomerate, suited for use in direct compression tableting techniques. U.S. Pat. No. 4,352,821 to Doran et al. discloses a binding and diluting agent consisting of fructose and a water insoluble carrier consisting of an edible, inorganic salt. U.S. Pat. No. 4,159,345 to Takeo et al. discloses an excipient consisting essentially of microcrystalline cellulose having certain characteristics.

C. Use of Xylitol in Tablet Contexts

Xylitol is not considered to be directly compressible, i.e. crystalline xylitol cannot be compressed into tablets of sufficient hardness and low friability. Therefore, in order to utilize xylitol in tablets, a variety of approaches to impart these characteristics have been used, without complete success.

One method has been to compress xylitol into tablets of relatively low initial hardness (e.g. about 6 S.C.U.) and "finish" the outer surface. The finishing step takes advantage of the unique crystallization properties of xylitol and its low melting point. Basically, the compressed tablets—which have a low initial hardness—are heated by exposing the surface of the tablets to hot air at temperatures greater than 94° C. which cause a phase change in the xylitol from solid to liquid. After cooling, recrystallization occurs quickly and a "glass" hard surface layer is formed. This finishing step, however, adds another significant step to the production process (thereby increasing the cost and decreasing the efficiency), cannot be used in all tablet contexts, and does not result in a tablet with uniform hardness.

Tablets can be formed with xylitol by means of the conventional wet granulation process with gelatin or starch as an additive. Xylitol has also been admixed with other polyols to form a mixture which is then compressed. U.K. Patent No. 1,526,020 to Lifesavers, Inc. discloses a process for the preparation of a tablet containing xylitol utilizing direct compression techniques. In the examples of the patent specification (which disclose the use of xylitol in combination with at least one other polyol), the ratio of xylitol/ sorbitol is 1:1 to about 0.43:1 (256:297), and the ratio of xylitol/mannitol is also 1:1. As a consequence, the examples enable only a partial utilization of the anti-cariogenic affect, and advantageous flavoring properties of xylitol, because a major portion of the tablet consists of sorbitol which does not show xylitol's taste and anti-cariogenic qualities.

From a technical perspective, the use of crystalline xylitol produces tablets which are too coarse in many contexts which give rise to a gritty texture and undesirable mouthfeel. The use of milled xylitol (less than 200 micron average particle size) produces a dry blended product (with sorbitol, for example) wherein flowability of the blend is extremely poor (near zero). Tableting machinery equipped with a force feeder is required. Dry blended xylitol and sorbitol is not an acceptable commercial alternative.

The present invention, however, discloses a free flowing, compressible granulate which comprises at least 94% to 98% by weight of xylitol in combination with another physiologically accepted polyol, preferably sorbitol. Sorbitol does not diminish the cooling effect of xylitol (as other constituents may) and also acts as a lubricant in the direct compression context. The granulate is suitable for use as a binding or diluting agent in direct compression techniques. The present invention also contemplates a method for producing such a xylitol-based granulate.

SUMMARY OF THE INVENTION

The present invention contemplates a free flowing, compressible granulate which comprises about 94% to about 98% by weight of xylitol, about 1% to about 5% by weight of a physiologically acceptable polyol other than xylitol, and less than about 1% by weight of water. The polyol does not contribute appreciable moisture to said granulate, nor does it negatively affect the taste profile of xylitol. In a particularly preferred embodiment, the free flowing, compressible granulate comprises about 95% to about 98% by weight of xylitol, about 1.5% to about 3.5% by weight of a physiologically acceptable polyol other than xylitol, and less than about 0.5% by weight of water. The physiologically acceptable polyol of choice is sorbitol, and other polyols such as mannitol, lactitol, maltitol and isomalt can also be used. If sorbitol is utilized, the present invention also contemplates a composition which comprises xylitol, sorbitol and less than about 2% of a physiologically acceptable polyol or polyols other than sorbitol, e.g. mannitol, which does not contribute appreciable moisture, or negatively affect the taste profile of xylitol.

Preferably, the bulk density of the composition of the present invention is between about 0.7 g/cm$^3$ and about 0.8 g/cm$^3$. The average particle size is between about 0.1 mm and about 1.0 mm. The composition exhibits good flow properties, preferably exhibiting a flow range with a maximum of about 15 s/100 g.

The present invention also contemplates a method for the production of a free flowing, compressible granulate wherein finely ground xylitol crystals are agglomerated with a polyol based syrup to obtain granules which are subsequently dried to a water content of less than about 1% by weight. The polyol does not contribute an appreciable amount of moisture, nor does it negatively affect the taste profile of xylitol. The composition, in a preferred embodiment, comprises about 94% to about 98% by weight of xylitol and between about 1% and about 5% by weight of a physiologically acceptable polyol with water present in amounts of less than 1% by weight. In a preferred embodiment of the method of the present invention, the ground xylitol has a particle size of about 0.01 mm to about 0.10 mm, with at least about 50% of said xylitol particles within that range. In a particularly preferred embodiment, the average particle size of the xylitol is about 0.07 mm, with at least about 50% of said xylitol having a particle size of between about 0.02 mm to about 0.10 mm.

The polyol based syrup used for the agglomerating step preferably is based on sorbitol, with a syrup containing between about 50% and about 85% of sorbitol by weight being particularly preferred.

DETAILED DESCRIPTION OF THE PREFERRED EMBODIMENT

A. General

The binding and diluting agent of the present invention is a granulated product which has a good flowability and which is prepared by agglomerating crystalline xylitol (ground or otherwise comminuted to a small particle size) by means of polyol based syrup wherein said polyol is a physiologically acceptable polyol other than xylitol. The xylitol is mixed with the syrup at a great speed to obtain a granular product; the granules are subsequently dried to a water content less than 1.0% by weight. The concentration of the physiologically acceptable polyol based syrup is selected so that the obtained granular product contains between about 94% and 98% by weight of xylitol and about 1% to 5% by weight of said physiologically acceptable polyol (other than xylitol). The preferred physiologically acceptable polyol is sorbitol because it does not negatively affect the taste profile of xylitol. The granular product may also contain physiologically acceptable polyols other than xylitol and sorbitol, preferably less than about 2% by weight, provided such polyols do not contribute appreciably to the moisture content, or negatively affect the taste profile of xylitol.

The flowability of the present invention agent can be measured by allowing a sample (200 g) to flow through a hopper (runner pipe dimensions: diameter 8 mm and length 25 mm) on to a balance connected to a recording device. The flowability (s/100 g) of the substance can thus be calculated from the curve so obtained. The flowability should ideally be better than 15 s/100 g. Another procedure for evaluating flowability is the determination of angle of repose: a sample (50 g) is passed slowly through a hopper on to a paper, and the angle defined between the paper and the formed hill is measured. This angle should not exceed 32°.

The bulk density of the substance can be measured by weighing a sample of about 300 g into a measuring cylinder. The sample is poured carefully into the cylinder; the sample is weighed accurately and its volume is recorded. The loose density (LD) can be calculated from this data. Thereafter the sample is vibrated at an amplitude of 1.5 mm, until it does not pack to a smaller volume. The volume is recorded, and the bulk density (also known as tapped density or "TD") is calculated.

Xylitol used as raw material in the production of the binding and diluting agent according to the invention has a purity exceeding 95% by weight, and has been ground or otherwise comminuted to an average particle size of between 0.01 mm to 0.10 mm by means of a suitable mill, such as a hammer mill common in the sugar industry to produce icing sugar.

In a preferred embodiment, sorbitol is added to the xylitol at the granulation stage in the form of sorbitol syrup which may be e.g. hydrogenated starch syrup containing about 50% to 90% by weight of sorbitol on dry substance basis, the remainder consisting of other sugar alcohols. Pure dissolved sorbitol is also suitable for use. Sorbitol syrup is diluted before granulation so that the dry substance content of the solution suits the granulation device. The nozzle structure of the Schugi device, for instance, requires a dry content below 50% by weight. The dry substance content of a commercial sorbitol syrup generally varies from 69% to 71% by weight. The dilution is preferably carried out with water, though a mixture of water and ethanol is also possible. The use of ethanol, however, is restricted by the poor solubility of sorbitol in ethanol.

A preferred method for preparing the present invention consists of granulating the ground or comminuted xylitol together with a small amount of sorbitol syrup by means of a suitable granulation device. The product is dried rapidly in a fluidized bed, for instance. Suitable granulation devices are well known in the art. The dryer may be separate, or the drying may be carried out in a granulator, depending on the type of device. In the granulation device, the ground or comminuted xylitol and the sorbitol syrup added evenly thereto are brought into a rapid movement which effects the agglomeration of the substance together with a small amount of syrup. The grain size can be adjusted by the mixture ratios and the mixing efficiency.

The granulated product is dried rapidly e.g. in a fluidized bed by means of dry air so that the final moisture content is below about 1% by weight, preferably below about 0.5% by weight. A suitable particle size is between about 0.1 mm to about 1 mm whereby about 99% of the granules are within this range. As used herein the term "dry air" refers to air with a water content no more than 7.5 grams of water per cubic meter of air, measured at 20° C.

The product obtained according to the invention is a freely flowing, compressible composition which has excellent compressibility and which withstands storing without getting cloddy. The preferred range of properties for one embodiment are as follows:

| | |
|---|---|
| Moisture content | less than about 1% by weight, with less than 0.5% by weight being particularly preferred |
| Average grain size (diameter) | about 0.1 mm to about 0.6 mm |
| Xylitol | about 95% to about 98% by weight |
| Sorbitol | about 2% to about 3% by weight |
| Other polyols | less than about 2% by weight |
| Bulk density (TD) | about 0.7 to about 0.8 g/cm³ |
| Flowability | maximum of about 15 s/100 g (a hopper with a pipe diameter of 8 mm and a pipe length of 25 mm), or flow angle of maximum 32° |

The granulation process is fundamentally different from the dry mixing of two polyols such as xylitol and sorbitol, such as that disclosed by G. B. Patent Nos. 1,526,020. The granulation process results in the crystallization of some of the sorbitol or present onto the surface of the xylitol particles forming fine, needle like protrusions. These needle like protrusions can be seen by electron microscopes, and a photograph showing the granulate of the present invention (with xylitol present in an amount of about 97% by weight, and sorbitol present in an amount of about 3% by weight) is shown in FIG. 1; the needle like crystals can be clearly seen. It is thought that the needle like protrusions are, or at least contribute to, the compressibility of the granulate of the present invention. Blends of xylitol and sorbitol in the proportion covered by the present invention which are simply admixed do not exhibit adequate compressibility and do not exhibit the needle like protrusions in electron micrographs such as those seen in FIG. 1. In order to obtain adequate compressibility with a xylitol/sorbitol admixture, it is necessary to increase the concentration of sorbitol.

Tablets made from pure crystalline xylitol show extremely poor hardness. At a force of 25 kN, 100% xylitol tablets exhibited a crushing strength less than 25N. Only when sorbitol was present in amounts exceeding 40% by weight did the crushing strength exceed 100N at a crushing strength of 25 kN. The present invention allows the use of high concentrations of xylitol thereby taking full advantage of its taste, metabolic and other advantages.

EXAMPLE 1

Production of Xylitol Powder

Crystalline xylitol (purity over 95% by weight) was ground by means of a turbo mill (Bauermeister, manufacturer Gebr. Bauermeister & Co., Hamburg, West Germany) to an average particle size of about 0.07 mm. Over 50% of the particles were within the range from about 0.02 mm to about 0.10 mm, and the powder did not contain any particles exceeding 0.125 mm, nor a dusty fraction.

EXAMPLE 2

Granulation of Xylitol Powder

A xylitol powder produced according to Example 1 and a 40% by weight sorbitol syrup solution (containing 34% by weight of sorbitol, and less than 5.7% of other polyols) were introduced into a granulator (Schugi, manufacturer Schugi, BV, Lelystad, Holland) at a speed of 800 kg/hour (powder) and 50 l/hour (syrup solution) at a temperature of 60° C. The spraying pressure was 2 bar and the rotative velocity 3,000 r/min, whereby grains having an average diameter of 0.42 mm were obtained (over 50% within the range of 0.2 to 0.6 mm). The resultant grains were dried with a fluidized-bed dryer (Schugi, manufacturer Schugi, BV, Lelystad, Holland). Granulate was fed into the dryer at a rate of 820 kg/h, and 10,000 m³/hour of dry air was introduced therein. The temperature of the drying air in the first quarter of the dryer was 45° C. and in the second quarter 35° C.; in the last two quarters of the dryer the temperature was room temperature, i.e. 20° C. to 25° C. The moisture content of the product was about 0.3% by weight, and the bulk density (TD) was about 0.74 g/ml.

The composition of the product was as follows:

| | |
|---|---|
| Xylitol | 97% |
| Sorbitol | 2% |
| Other Polyols | approx. 1% |
| Moisture | 0.3% |

The flowability of the granulate produced according to Example No. 2 was extremely good (flow rate 12 s/100 g; flow angle 30°), and the properties of the granulate did not change during storage (75 days, 18° C.).

EXAMPLE 3

Compression of Tablets

The granulate produced according to Example 2 was compressed to tablets by means of an eccentric press (Korsch EK-O/DMS; manufacturer Korch OHC Maschinenfabrick, Berlin, West Germany). Magnesium stearate (1%) was used as an additive. The diameter of the tablet was 11 mm and weight 500 mg. The crushing strength of tablets manufactured by different compression forces was determined in accordance with the instructions of the European Pharmacopean. The results are shown in Table 1.

TABLE I

| Compression Force | Crushing Strength |
|---|---|
| 5 kN | 46 N |
| 10 kN | 66 N |
| 15 kN | 88 N |
| 20 kN | 108 N |

EXAMPLE 4

Compression of Tablets

A granulate produced according to Example 2 was compressed to double-convex tablets by means of a rotation machine (Manesty D 3; manufacturer, Manesty Machines, Liverpool, England). Magnesium stearate (1%) was used as an additive. The diameter of the tablet was 15 mm and weight 907 mg. The crushing strength of the tablet (European Pharmacopea) was 127N; the weight loss in friability tests was 0.71%.

Tablets prepared in Examples 3 and 4 had acceptable mouthfeel, initial hardness and friability.

The foregoing general discussion and experimental examples are intended to be illustrative of the present invention, and are not to be considered as limiting. Other variations within the spirit and scope of this invention are possible, and will present themselves to those skilled in the art.

We claim:

1. A free flowing, compressible granulate comprising:
   94% to 98% by weight of xylitol,
   1% to 5% by weight of another physiologically acceptable polyol which will not contribute appreciable moisture to said granulate, and will not appreciably negatively affect the taste profile of xylitol, and
   less than 1% by weight of water.

2. The granulate of claim 1 wherein said granulate comprises 95% to 98% by weight of said xylitol, 1.5% to 3.5% by weight of said polyol, and less than 0.5% by weight of said water.

3. The granulate of claim 2 wherein
   said polyol is selected from the group consisting of mannitol, lactitol, maltitol and isomalt.

4. The granulate of claim 2 wherein said physiologically acceptable polyol is sorbitol.

5. The granulate of claim 4 which comprises an additional physiologically acceptable polyol or combination thereof which will not contribute appreciable moisture to said granulate, or appreciably negatively affect the taste profile of the xylitol present up to 2% by weight.

6. The granulate of claim 4 wherein the bulk density thereof is between 0.7 g/cm$^3$ and 0.8 g/cm$^3$.

7. The granulate of claim 4 wherein the average particle size is between 0.1 mm and 1 mm.

8. The granulate of claim 4 wherein the flowability thereof is less than 15 s/100 g.

9. The granulate of claim 5 wherein said polyol or combinations thereof are selected from the group consisting of mannitol, lactitol, maltitol and isomalt.

* * * * *